United States Patent [19]

Ladd et al.

[11] Patent Number: 4,482,572

[45] Date of Patent: Nov. 13, 1984

[54] 1-ACYLAMINO-1-CYCLOPENTANECAR-BOXYLIC ACIDS

[75] Inventors: David L. Ladd, Overbrook Hills; Joseph Weinstock, Phoenixville, both of Pa.

[73] Assignee: SmithKline Beckman Corporation, Philadelphia, Pa.

[21] Appl. No.: 491,619

[22] Filed: May 5, 1983

[51] Int. Cl.$^3$ ................. A61K 31/195; C07C 103/737
[52] U.S. Cl. .................................... 424/319; 562/502; 562/504
[58] Field of Search ................. 562/502, 504; 424/319

[56] References Cited

U.S. PATENT DOCUMENTS 2,917,490  12/1959  Caldwell et al. .................... 562/502
4,105,789   8/1978  Ondetti et al. ...................... 424/319

OTHER PUBLICATIONS

D. W. Cushman et al., Biochemistry, 16, 5484, (1977).

Primary Examiner—Natalie Trousof
Assistant Examiner—Patricia M. Scott
Attorney, Agent, or Firm—William H. Edgerton; Richard D. Foggio; Alan D. Lourie

[57] ABSTRACT

1-Acylamino-1-cyclopentanecarboxylic acids have been prepared by acylation of certain 1-amino-1-cyclopentanecarboxylic acids and found to have renal vasodilating and diuretic properties.

8 Claims, No Drawings

1-ACYLAMINO-1-CYCLOPENTANECARBOXYLIC ACIDS

This invention relates to a new group of 1-acylamino-1-cyclopentanecarboxylic acids which improve kidney function. More specifically, these compounds are renal vasodilators and diuretic agents.

BACKGROUND OF THE INVENTION

The prior art recognizes that improvement of any parameter of kidney function, such as inducing natriuresis or improving blood flow through the kidney by decreasing renal vascular resistance, is an important component of the medical treatment of either hypertension and kidney dysfunction.

D. W. Cushman et al., Biochemistry, 16 5484 (1977), reported that a number of N-acylprolines were potent inhibitors of angiotensin converting enzyme. Receptor site requirements were alleged to be responsible for the specificity of structure necessary in that series for ACE inhibition.

The compounds of this invention are believed to be novel in structure and in biological activity.

DESCRIPTION OF THE INVENTION

The chemical structures of the compounds of this invention are illustrated by the following formula:

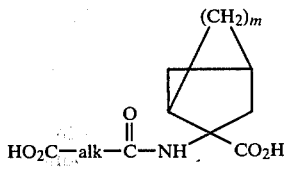

in which:
m is 0 or 2, and
alk is a straight or branched alkylene of 1-4 carbons.

A subgeneric group of this invention are those compounds with structures represented by formula I in which m is 0. The preferred alkylene chain is ethylene.

The pharmaceutically acceptable salts of the compounds of formula I, prepared as known to the art with nontoxic organic and inorganic bases, are also a part of this invention. Such salts are the nontoxic alkali metal salts, for example, calcium, sodium or potassium salts, ammonium salts or salts with nontoxic organic bases such as those with triethylamine or butylamine.

The compounds are prepared from known starting materials such as 1-amino-1-cyclopentanecarboxylic acid or 2-amino-bicyclo[2.2.1]heptane-2-carboxylic acid, usually by reaction of the amino acid with a carboxylic anhydride in the presence of an acid binding agent with a solvent. Reaction in refluxing dry pyridine is useful. Alternatively, the 1-aminocyclopentanecarboxylic acid, with the acid group blocked as known in the peptide art, is reacted with a half ester of a dicarboxylic acid in the presence of an amide-forming coupling agent, for example, dicyclohexylcarbodiimide or the N-hydroxysuccinimide ester. The blocking groups are then removed by standard chemical reactions.

The compounds of this invention have been demonstrated to have biological activity in the anesthetized dog protocol which is known to the art as a test for renal vasodilator activity and in the spontaneously hypertensive rat protocol, for diuretic activity. As examples of these biological activities: 1-succinylamino-1-cyclopentanecarboxylic acid had an $ED_{15}$ of 239 $\mu g/kg$ in the dog protocol (dopamine, $ED_{15}$ is 3.5 $\mu g/kg$) and increased urine volume and excretion of sodium at 25 and 50 mg/kg intraperitoneally in the SHR protocol. 2-Succinylaminobicyclo[2.2.1]heptane-2-carboxylic acid increased blood flow and decreased vascular resistance significantly at 3, 30 and 300 $\mu g/kg/min$ in the dog and increased urine volume and sodium excretion at 50 mg/kg in the rat.

Pharmaceutical compositions which use the compounds of this invention as active ingredients and which have pharmacodynamic activity within the kidney, for example, renal vasodilation and diuretic activity, are prepared in conventional dosage unit forms by incorporating a compound of formula I, or a pharmaceutically acceptable base addition salt thereof, into a pharmaceutical carrier, according to accepted pharmacy procedures. A nontoxic quantity is used which is sufficient to produce the desired pharmacodynamic activity in an animal to human subject. Preferably, the compositions will contain the active ingredient in a biologically active but nontoxic quantity selected from the range of about 100 mg to about 500 mg, preferably about 150–300 mg, of active ingredient, calculated as the base, per dosage unit. This quantity depends on the relative potency of the base compound compared with that of the prototypic species, described first above, as well as on the specific biological activity desired, the route of administration, that is, whether oral or parenteral, and the condition and size of the patient.

The pharmaceutical carrier employed for the dosage units is, for example, either a solid or liquid. Exemplary of solid carriers are lactose, terra alba, sucrose, talc, gelatin, agar, pectin, acacia, magnesium stearate or stearic acid. Exemplary of liquid carriers are isotonic saline for parenteral use as well as syrup, peanut oil, olive oil or water for soft gelatin capsules. Similarly, the carrier or diluent may include a time delay material, for example, glyceryl monostearate or glyceryl distearate alone or admixed with a wax. Such sustained release products as well as pro-drug derivatives which may be gradually metabolized to the active parent are employed to prolong the biological activity of the compounds of this invention.

A wide variety of pharmaceutical forms is optionally employed. Thus, if a solid carrier for either oral or rectal admnistration is used, the mixed preparation can be, respectively, tableted or placed in a hard gelatin capsule in powder or sustained release pellet form, in the form of a troche or lozenge or in a suppository. The amount of solid carrier will vary widely but, preferably, will be from about 25 mg to about 1 g. If a liquid carrier is used, the preparation will be in the form of a syrup, emulsion, soft gelatin capsule, sterile injectable liquid, such as an ampul, a concentrate for infusion or an aqueous or nonaqueous liquid solution or suspension for oral administration.

The method for producing improvement in kidney function manifests itself by inducing renal vasodilation, anti-hypertensive and diuretic activity. It comprises administering orally, rectally or parenterally to a subject in need of such activity a compound of formula I or a pharmaceutically acceptable salt thereof, usually combined with a pharmaceutical carrier, in a nontoxic amount sufficient to produce said activity. The route of administration may be any route which effectively transports the active compound to the renal system receptors which are to be stimulated. Such routes include oral, rectal or parenteral administration, the oral route being preferred. Parenteral administration may be subcutaneous or, preferably, intravenous for critical use.

Advantageously, doses selected from the dosage unit ranges given above will be administered several times, such as from one to five times, a day. The daily dosage regimen is selected from the range of about 300 mg to about 1.0 g.

The following examples are designed solely to illustrate the preparation and use of the compounds of this invention. The temperatures are Centrigrade. Other variations of these examples will be obvious to those skilled in the art.

EXAMPLE 1

A mixture of 5.00 g (0.0387 mol), Beil. 14 (1) 526, of 1-amino-1-cyclopentanecarboxylic acid, 3.87 g (0.0387 mol) of succinic anhydride and 50 ml of dry pyridine was heated under reflux for 1.75 hours. The resultant mixture was filtered while still warm and volatiles were removed from the filtrate under reduced pressure to leave a tan oil. The oil was dissolved in water and passed through a column containing 100 g of acidic polystyrene ion-exchange resin (AG-50W-X8, Bio-Rad Laboratories). The column ws eluted with water until the eluent no longer tested acidic. The acidic eluent was concentrated at 65° to give 7.52 g (85%) of oily 1-succinylamino-1-cyclopentanecarboxylic acid. Crystalline white product was obtained after two crystallizations from hot ethyl acetate, mp: 129°–131°.

The acid (500 mg) is dissolved in dry ether and a small nugget of potassium metal is added. The dipotassium salt separates and is washed and dried.

EXAMPLE 2

1-Glutarylamino-1-cyclopentanecarboxylic acid was prepared in 53% yield as described for the succinyl analog in Example 1 to give a white solid, mp: 183°–5° from ethyl acetate.

EXAMPLE 3

A mixture of 4.58 g (0.0209 mol) of 1-amino-1-cyclopentanecarboxylic acid benzyl ester, 6.75 g (0.050 mol) of 1-hydroxybenzotriazole and 65 ml of dry tetrahydrofuran was cooled in an ice bath and treated with 4.00 g (0.025 mol) of 4-methoxycarbonyl-2-methylbutyric acid and 13.1 ml (0.025 mol) of 1.91 M dicyclohexylcarbodiimide in tetrahydrofuran. The mixture was stirred for 1 hour at 0°, then, overnight at room temperature. The mixture was filtered and the volatiles were removed under reduced pressure. The resultant residue was taken up in ethyl acetate which was, then, washed twice with 10% acetic acid, once with water, twice with 5% sodium bicarbonate solution and once with brine. The ethyl acetate extract was, then, dried over anhydrous sodium sulfate and concentrated to give 7.04 g of the methyl, benzyl ester of 1-[(4-carboxy-2-methylbutanoyl)amino]-1cyclopentanecarboxylic acid. Purified ester was obtained as a yellow oil by chromatography over silica gel eluting with chloroform containing up to 5% methanol.

A solution of 6.05 g (0.0167 mol) of di-ester in 125 ml of acetone containing 0.50 g of 10% palladium-on-charcoal was hydrogenated at room temperature at an initial pressure of 60 psi. The resultant mixture was filtered and the filtrate concentrated to an oil which was converted to 4.89 g of the dicyclohexylamine salt in acetonitrile. A solution of 4.89 g (0.0108 mol) of the salt and 32.4 ml of 1.0 N sodium hydroxide solution (sufficient methanol added to give solution) was stirred overnight at room temperature, then, concentrated under reduced pressure to remove the alcohol. The dicyclohexylamine layer which separated was discarded. The aqueous layer was passed through a column of 112 g of AG-50W-X8 resin. The column was eluted with water until the eluent no longer tested acidic. The acidic eluent was concentrated to give 2.46 g of semi-solid 1-[(4-carboxy-2-methylbutanoyl)amino]-1-cyclopentanecarboxylic acid which was recrystallized from hot ethyl acetate, mp: 169.5°–171.5°.

EXAMPLE 4

1-[(3-Methoxycarbonyl-2-methylpropanoyl)amino]-1-cyclopentanecarboxylic acid, benzyl ester was prepared as described in Example 3 from 10.96 g (0.050 mol) of 1-amino-1-cyclopentanecarboxylic acid, benzyl ester and 7.31 g (0.050 mol) of 3-methoxycarbonyl-2-methylpropionic acid. Crude di-ester crystallized to give 13.57 g (78%) of an off-white solid, mp: 88°–93°. This was used without further purification.

A solution of 11.29 g (0.0325 mol) of di-ester in 200 ml of acetone which contains 0.9 g of 10% palladium-on-charcoal was hydrogenated at room temperature at an initial pressure of 60 psi for 1 hour; an additional 0.25 g of catalyst was added and hydrogenation was continued for an additional 80 minutes. The resultant mixture was filtered and the filtrate concentrated to give 8.38 g (100%) of white product. Recrystallization from toluene afforded purified half-ester, mp: 119°–122.5°.

A mixture of 5.27 g (0.0205 mol) of this product salt and 61.4 ml (0.0614 mol) of 1.0 N sodium hydroxide solution was stirred overnight at room temperature. The resultant solution was passed thru a column containing 211 g of AG-50W-X8 resin, then, worked up as previously described to give 4.84 g (97%) of 1-[(3-carboxy-2-methylpropanoyl)amino]-1cyclopentanecarboxylic acid as a white solid which was recrystallized from ethyl acetate, mp: 169°–170°.

EXAMPLE 5

A mixture of 1.00 g [6.09 mmol, J. Biol. Chem., 244 1510 (1969)]of 2-amino-2norbornanecarboxylic acid hemihydrate (mixture of endo and exo isomers), 0.61 g (6.09 mmol) of succinic anhydride and 25 ml of dry pyridine was heated under reflux for 2 hours. The resultant solution was concentrated under reduced pressure to leave an oil which was treated with 50 ml of 10% hydrochloric acid, then, sufficient concentrated acid to acidify. The acidic mixture was extracted three times with ethyl acetate. The combined extracts were washed with 10% hydrochloric acid, then, concentrated to give 0.48 g of white solid 2-succinylamino-bicyclo[2.2.1]-heptane-2-carboxylic acid. The acidic solution from above was combined with the acidic washing and concentrated to a white solid (product plus pyridine hydrochloride). This solid was dissolved in 20 ml of water and extracted three times with ethyl acetate. The combined organic extracts were dried and concentrated to give 0.38 g of white solid 2-succinylaminobicyclo-[2.2.1]heptane-2-carboxylic acid. The two crops of product were combined and recrystallized from the ethyl acetate to yield 0.48 g (31%) of amide, mp: 182.5°–184.5°.

EXAMPLE 6

1-Succinylamino-1-cyclopentanecarboxylic acid (300 mg) is mixed with 100 mg of lactose and 2 mg of magnesium stearate. The mixture is filled into a hard gelatin capsule, then, administered orally four times daily to a patient in need of diuretic activity.

What is claimed is:

1. A compound of the structural formula:

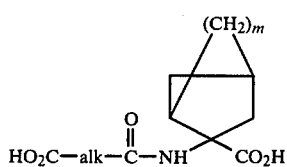

in which:
 m is 0 or 2, and
 alk is alkylene of 1-4 carbons; or a pharmaceutically acceptable salt thereof with a nontoxic organic or inorganic base.

2. The compound of claim 1 in which m is 0 and alk is ethylene which is 1-succinylamino-1-cyclopentanecarboxylic acid or a pharmaceutically acceptable salt thereof.

3. The compound of claim 1 which is 1-succinylamino-1-cyclopentancarboxylic acid in free acid form.

4. The compound of claim 1 in which m is 2 and alk is ethylene which is 2-succinylaminobicyclo[2.2.1]heptane-2-carboxylic acid.

5. The compound of claim 1 in which m is 0 and alk is propylene which is 2-glutarylamino-1-cyclopentanecarboxylic acid.

6. The compound of claim 1 in which m is 0 and alk is

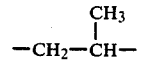

which is 1-[(3-carboxy-2-methylpropanoyl)amino]-1-cyclopentanecarboxylic acid.

7. A pharmaceutical composition for inducing renal vasodilation, anti-hypertensive and diuretic activity comprising a nontoxic, effective therefor quantity of a compound of claim 1 and a pharmaceutical carrier.

8. The method of inducing renal vasodilation, anti-hypertensive and diuretic activity in a patient in need thereof comprising administering orally, rectally or parenterally to said patient a quantity of a compound of claim 1 which is nontoxic and effective therefor.

* * * * *